United States Patent [19]

D'Errico

[11] 4,172,296
[45] Oct. 30, 1979

[54] BICENTRIC JOINT PROSTHESIS

[75] Inventor: Joseph D'Errico, Clifton, N.J.

[73] Assignee: Howmedica, Inc., New York, N.Y.

[21] Appl. No.: 874,244

[22] Filed: Feb. 1, 1978

[51] Int. Cl.² .............................................. A61F 1/24
[52] U.S. Cl. ........................................ 3/1.912; 3/1.91;
3/1.913; 128/92 C; 128/92 CA
[58] Field of Search ................................. 3/1.9–1.913;
128/92 C, 92 CA

[56] References Cited
U.S. PATENT DOCUMENTS

| | | | |
|---|---|---|---|
| 3,698,017 | 10/1972 | Scales et al. | 3/1.912 |
| 3,813,699 | 6/1974 | Giliberty | 3/1.912 |
| 3,816,854 | 6/1974 | Schlein | 3/1.91 |
| 3,842,442 | 10/1974 | Kolbel | 3/1.91 |
| 3,863,273 | 2/1975 | Averill | 3/1.91 |
| 3,978,528 | 9/1976 | Crep | 3/1.912 X |
| 4,044,403 | 8/1977 | D'Errico | 3/1.91 X |

*Primary Examiner*—Ronald L. Frinks
*Attorney, Agent, or Firm*—Pennie & Edmonds

[57] ABSTRACT

A prosthesis for an artificial bicentric joint comprising a cup member encased in a metallic outer shell member, the cup member having an inner surface adapted for receiving the male prosthetic member of the articulating joint and an outer surface comprising a spherical zone terminating at its base in a right cylindrical zone, the altitude of the spherical zone being less than the spherical radius, and having an annular groove approximately at the junction of the spherical and cylindrical zones, the shell member having an outer surface adapted for implantation in a skeletal cavity and an inner surface, substantially congruent with the outer surface of the cup member, having detent means for engaging the annular groove of the cup member to permanently secure the cup member within the shell member.

8 Claims, 7 Drawing Figures

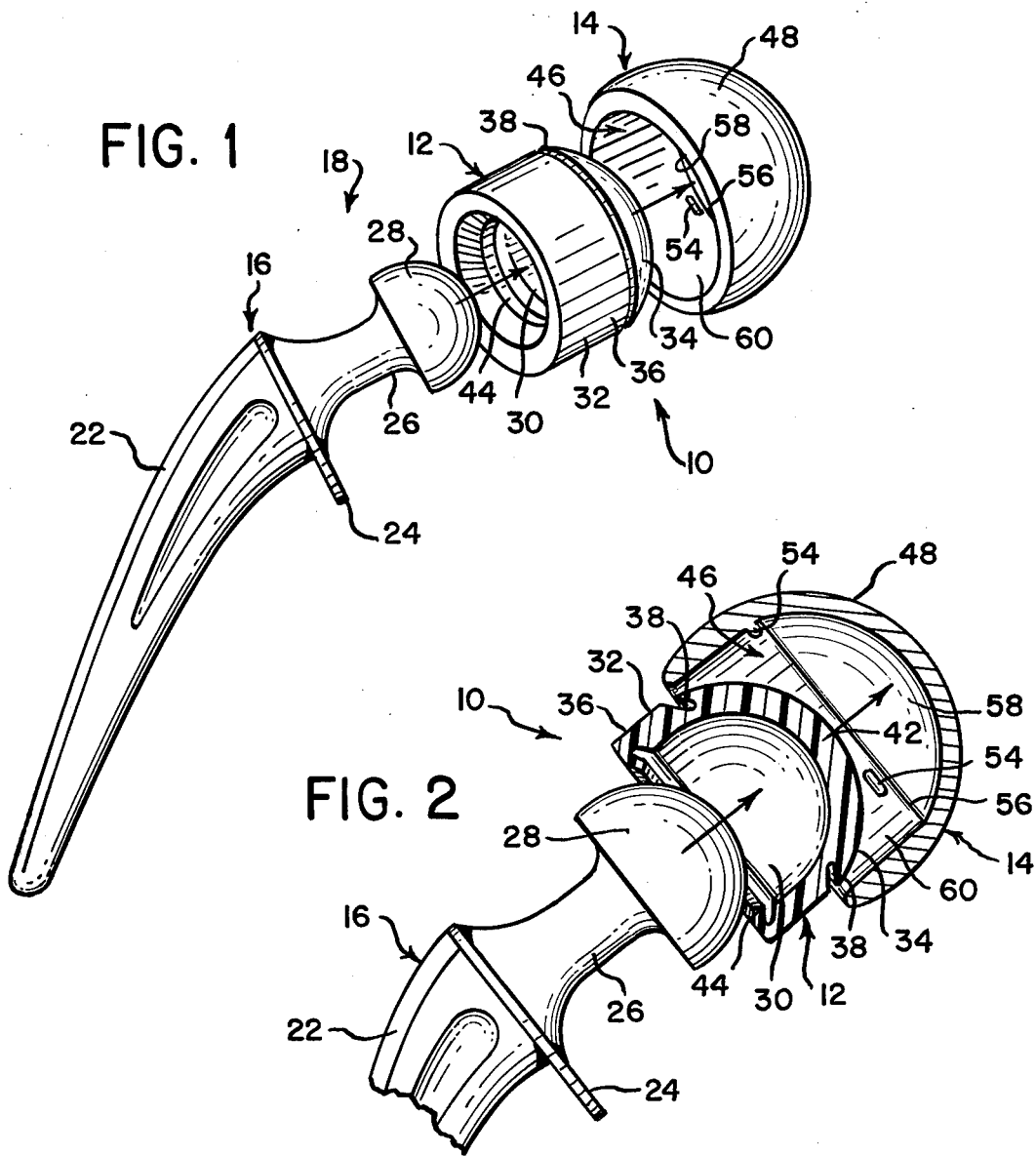
FIG. 1
FIG. 2
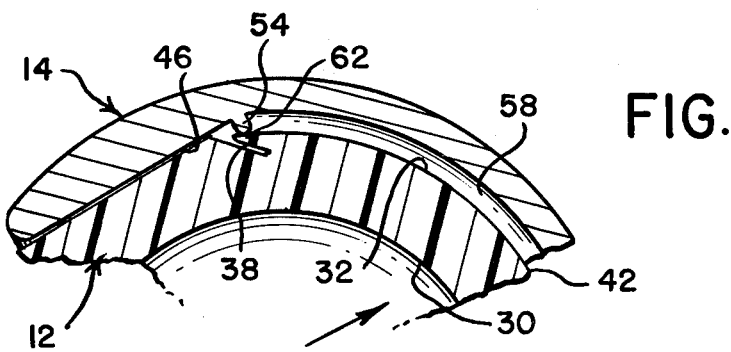
FIG. 3

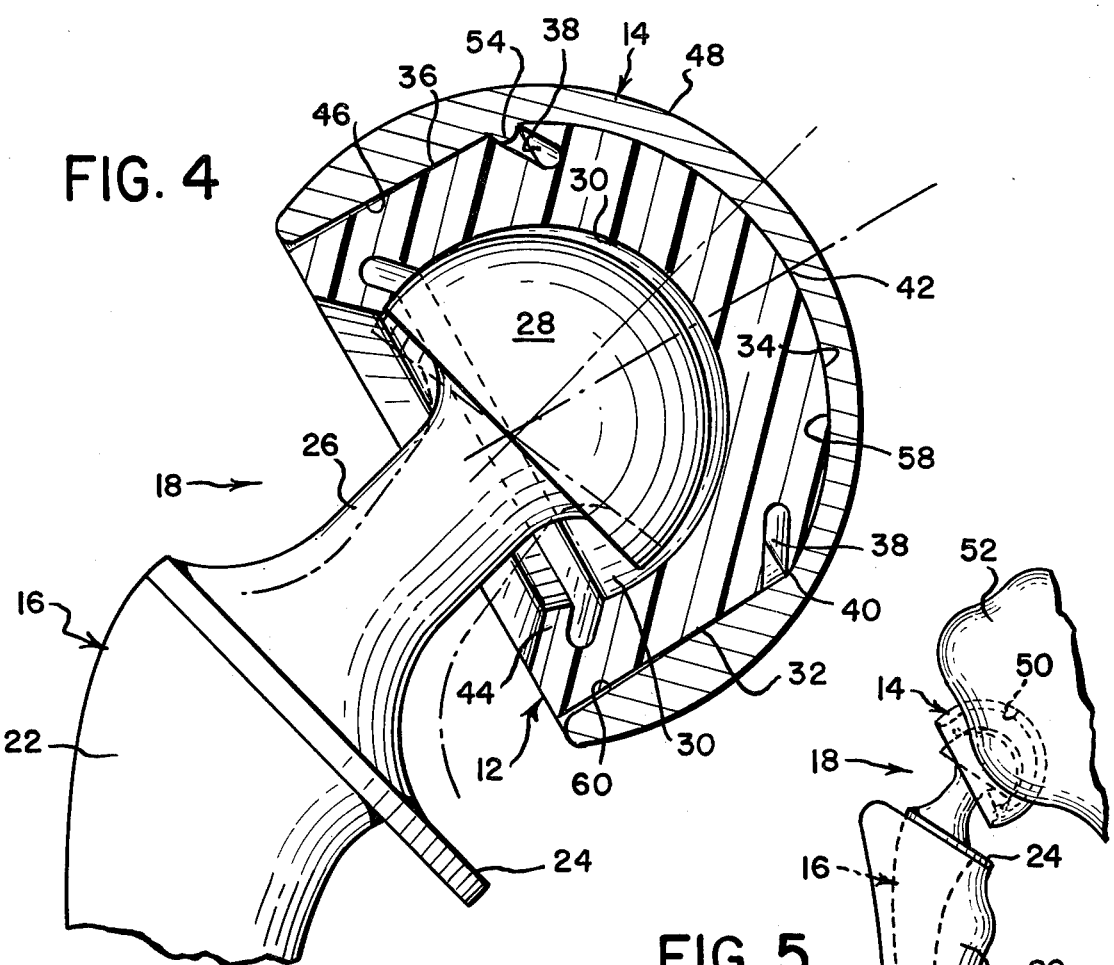
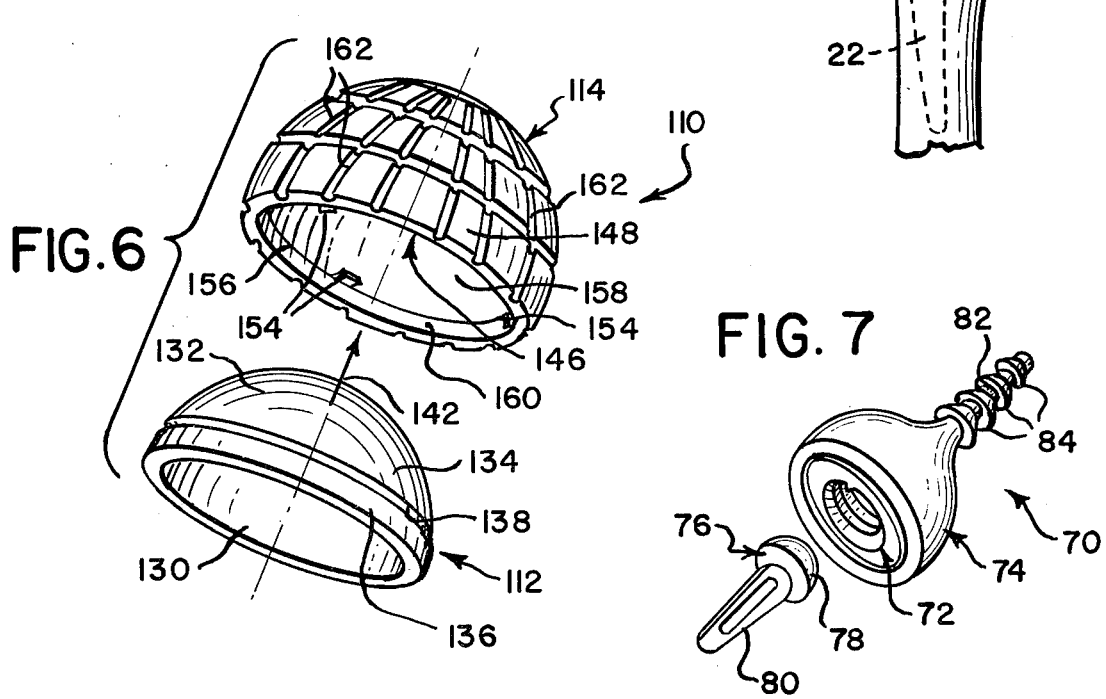

BICENTRIC JOINT PROSTHESIS

BACKGROUND OF THE INVENTION

This invention concerns artificial devices for implantation in the human body. More particularly, it concerns a prosthetic articulating joint.

The use of artificial devices implanted in the human body for replacing defective, damaged or diseased anatomical structures has long been known.

One form of such prosthetic devices replaces anatomical joints of the body having ball-and-socket characteristics such as, for example, the hip joint. This hip prosthesis essentially provides a detachable interconnection between the femur and acetabulum socket of the pelvis to accomplish the universal type movement associated with the replaced natural biological joint. Conventional prosthetic total hip joints normally comprise an acetabulum type cup member with a spherical cavity, which may be suitably secured in a variety of ways to the acetabulum socket of the pelvis, and an artificial femoral insert, which is appropriately attached to the femur. The femoral insert includes a smooth and substantially spherical head member which mates with, and is rotatably supported by, the spherical cavity of the cup member. As a result of this structural interrelationship, a ball-and-socket type joint is created which permits the ordinary type of articulated motion associated with the human hip joint.

Among the several known concepts for providing artificial articulated joints are prostheses utilizing bicentric action, such as those of U.S. Pat. No. 3,813,699 and 3,863,273 directed primarily to hip joints in which articulation can occur both between the head of the femoral insert and the cup member of the prosthesis and between the prosthesis and the acetabulum socket of the pelvis. While both of these prostheses are bicentric and embrace the concept of wear between plastic and metal rather than between metal and bone, neither device provides means whereby the head of the femoral insert is more easily inserted into than withdrawn from the spherical cavity of the acetabulum cup member so that the prosthesis is not subject to joint dislocation. Such means are provided in the prosthesis of U.S. Pat. No. 4,044,403. This prosthesis, however, in turn does not provide means for more suitably encasing the plastic cup member in its metallic outer shell.

It is therefore a primary objective of the present invention to provide a means whereby the plastic cup member of a bicentric joint prosthesis is easily inserted into and effectively retained by its metallic outer shell.

SUMMARY OF THE INVENTION

The prosthesis of the present invention comprises a cup member formed of resilient polymer encased in a metallic outer shell member. The cup member has an inner surface adapted to receive the male prosthetic member of an articulating joint and an outer surface comprising a spherical zone terminating at its base in a right cylindrical zone, the altitude of the spherical zone being less than the spherical radius; the outer surface of the cup member has an annular groove approximately at the junction of the spherical and cylindrical zones. The shell member has an outer surface adapted to be implanted in a skeletal cavity and an inner surface substantially congruent with the outer surface of the cup member, the inner shell surface having detent means for engaging the annular groove in the cup member to permanently secure the cup member within the shell member.

In preferred embodiments of the prosthesis, the inner cup surface comprises a spherical zone concentric with the outer spherical cup surface with an altitude greater than the spherical radius of the inner cup surface; the outer shell surface comprises a spherical zone concentric with the inner spherical shell surface with an altitude greater than the spherical radius of the outer shell surface; the annular groove in the cup member is canted toward the pole of the spherical zone of the outer cup surface; the detent means of the shell member comprises a plurality of projections distributed along the annular junction of the spherical and cylindrical zones of the congruent inner shell surface; the resilient polymer is ultra high molecular weight polyethylene; and the outer shell surface is adapted for implantation in the acetabulum. The outer shell surface may also comprise means to facilitate permanent attachment of the shell member to the skeletal cavity.

BRIEF DESCRIPTION OF THE DRAWINGS

The above and other objects, features and advantages of the present invention will be apparent from the appended detailed description of embodiments thereof in conjunction with the accompanying drawings wherein like reference numerals indicate like structures throughout the several views.

FIG. 1 is an exploded perspective view illustrating a hip joint prosthesis embodying the principles of the present invention;

FIG. 2 is a fragmented view, partly in section, clearly demonstrating in greater detail the components forming the bicentric hip joint prosthesis;

FIG. 3 is an enlarged fragmented view similar to FIG. 2 illustrating insertion of the cup member into the shell member during assembly of the prosthesis;

FIG. 4 is an enlarged fragmented view, partly in section, illustrating the cooperating connection between the assembled components;

FIG. 5 is a schematic view illustrating the hip joint prosthesis applied to the human body;

FIG. 6 is an exploded perspective view of another embodiment of the present invention and FIG. 7 is an exploded perspective view of a shoulder joint prosthesis embodying the principles of the present invention.

DESCRIPTION OF THE PREFERRED EMBODIMENTS

FIG. 1 depicts an implantable hip prosthesis embodying the principles of the present invention and designated generally by reference numeral 10.

As depicted in FIGS. 1 and 2, prosthesis 10 includes a cup member 12 and an outer shell member 14. In the assembled condition shown in FIGS. 4 and 5, these components together with femoral insert 16 constitute an artificial articulating anatomical joint, designated generally by reference numeral 18, for implantation in a human body to replace diseased, defective or damaged hip joints and provide substantially the same type of movement which would be normally associated with the natural hip joint.

Femoral insert 16 may be a suitable and conventional prosthetic device, such as that disclosed in U.S. Pat. No. 3,965,490, adapted to be implanted in the femur 20 through well-known medical procedures. When inserted into the femur 20, the femoral insert 16 is intended to generally assume the position depicted in FIG. 5. Femoral insert 16 comprises, in integral combination, shank portion 22, shoulder portion 24, neck portion 26 and head 28. The natural femur head, which may have been diseased, defective or damaged, will have been removed prior to the insertion of the femoral insert 16. Head 28 comprises a generally spherical configuration with a continuously smooth and highly polished external surface having low-friction characteristics. Such low-friction characteristics facilitate a smooth and continuous type of relative movement between femoral insert 16 and cup member 12. Femoral insert 16 is made of a conventional material suitable for implantation in body tissue including the anatomical bone structure. An example of such a material is Vitallium ®, the trademark of Howmedica Inc. for a cobalt-chromium alloy developed and used for cast dentures and for internal applications by surgeons. This alloy has the following characteristics: a specific gravity of 8.29, a tensile strength of 95,000 psi minimum; a 2 percent offset yield strength of 65,000 psi minimum; a modulus of elasticity of $30-32 \times 10^6$ psi and a Rockwell "C" hardness of 23–28. When polished, it is exceedingly smooth and permanently lustrous. Its outstanding qualities include chemical inertness in relation to living tissues and a high degree of resistance to corrosion.

Cup member 12 has an inner surface 30 adapted to receive femoral insert 16 and an outer surface 32 comprising a spherical zone 34 terminating at its base in a right cylindrical zone 36, the altitude of spherical zone 34 being less than the spherical radius. In addition, cup member 12 has an annular groove 38 in outer surface 32 approximately at the junction 40 of spherical zone 34 and cylindrical zone 36. As illustrated, annular groove 38 is preferably canted toward the pole 42 of spherical zone 34. Also as illustrated, the inner surface 30 of cup member 12 comprises a spherical zone which is concentric with spherical zone 34 of outer surface 32 and which has an altitude greater than the spherical radius of inner surface 30. The spherical radius of inner surface 30 is of such dimension as to snugly receive and support femoral head 28 in a centrally formed and substantially congruent cavity and thus provide for universal movement. In the embodiment of FIGS. 1–5, inner surface 30 has additionally an annular lip means 44, disclosed in detail in U.S. Pat. No. 4,044,403, which not only permits easy insertion of femoral insert 16 into cup member 12 but also prevents disengagement of these members in a positive and simple manner.

Cup member 12 is fabricated from a resilient polymer which is compatible for implantation in the human body. Additionally, the polymer should possess good strength, low-friction and high lubricity properties, since cup member 12 supports head 28 for universal movement during an extended period of time. Ultra high molecular weight polyethylene provides an extremely satisfactory material for this purpose, although other polymers having similar properties may be employed.

Cup member 12 is encased in metallic outer shell member 14, which has an inner surface 46 substantially congruent with the outer surface 32 of cup member 12 and an outer surface 48 adapted to be implanted in the acetabulum socket 50 of pelvis 52. The inner surface 46 of shell member 14 is provided with a plurality of projections 54 distributed along the annular junction 56 of spherical zone 58 and cylindrical zone 60 of inner surface 46 of shell member 14. While the depicted embodiment shows the projections 54 in the form of tabs, other projections and other detent means for engaging annular groove 38 to permanently secure cup member 12 within shell member 14 may also be employed.

Shell member 14 is fabricated from a metal possessing low-friction characteristics, sufficient strength to remain durable during repeated loadings and compatibility with body tissue. Such metal includes Vitallium ®, described hereinbefore, but other metals possessing such properties may be used.

During implantation of prosthesis 10 in acetabulum socket 50 of pelvis 52, acetabulum socket 50 is prepared in conventional surgical fashion to accomodate shell member 14. In such case, shell mumber 14 is not affixed to the acetabulum socket. In the embodiment illustrated in FIGS. 1–5, outer surface 48 of shell member 14 comprises a spherical zone concentric with spherical zone 58 of inner surface 46 and having an altitude greater than the spherical radius of outer surface 48. If free articulation within acetabulum socket 50 is desired, outer surface 48 of shell member 14 is highly polished. Limited articulation results with a less polished surface.

In other cases, permanent attachment of a bicentric prosthesis to the skeletal cavity may be desired. Such attachment can be effected with the embodiment of the present invention illustrated in FIG. 6. In this prosthesis, generally designated as 110, cup member 112 has an inner surface 130 for receiving a femoral head comprising a spherical zone concentric with spherical zone 134 of outer surface 132, the altitude of inner surface 130 being equal to or slightly less than the spherical radius, and an outer surface 132 with a relatively short right cylindrical zone 136.

Outer shell member 114 of prosthesis 110 has an inner surface 146 which is substantially congruent with the outer surface 132 of cup member 112 and is provided with tabs 154 distributed along the annular junction 156 of spherical zone 158 and cylindrical zone 160 for engaging annular groove 138 of cup member 112 to permanently secure cup member 112 within shell member 114; annular groove 138 is preferably canted at an angle of about 45 degrees toward pole 142 of spherical zone 134. The outer surface 148 of shell member 114 comprises a spherical zone concentric with spherical zone 158 with spaced annular depressions or grooves 162 which provide for cement fixation of prosthesis 110 within the acetabulum.

The interaction of the two members of the prosthesis of the present invention during assembly is illustrated in detail by FIG. 3 in connection with embodiment 10. As cup member 12 is inserted into outer shell member 14, tabs 54 of shell member 14 contact the hinge 62 of cup member 12 formed by annular groove 38 and that portion of outer surface 32 toward pole 42. Since cup member 12 is fabricated of resilient polymer, hinge 62 deflects inwardly toward groove 38 and permits tabs 54 to slide past hinge 62 and into groove 38. The outer surface 32 of cup member 12 is thus able to tightly contact the congruent inner surface 46 of shell member 14. Once cup member 12 has been fully inserted into shell member 14, the two members are permanently attached, since hinge 62 cannot slide past tabs 54. Thus easy insertion and effective retention of cup member 12 within shell member 14 is realized.

Although the foregoing description of primarily directed to a human hip joint, it should be emphasized that the spirit of this invention envisions its application in other articulating anatomical joints in both human and veterinary uses. Thus, the broader aspects of this invention contemplate its utilization in, for example, the shoulder joint shown in FIG. 7. Prosthesis 70 comprises cup member 72 and shell member 74. Implantable insert 76 has a substantially spherical head 78 with smooth and low-friction characteristics and a stem 80 adapted to be inserted in the appropriate anatomical shoulder structure. Shell member 74 is provided with an elongated stem 82 with a plurality of serrated projections 84 designed to secure the shell member 74 to a corresponding anatomical structure. Shell member 74 is also formed with an inner surface as in prostheses 10 and 110 which securely receives cup member 72, which is similar to cup member 12. The materials forming the above described shoulder prosthesis may be similar to that of the previously described embodiments, although other suitable materials consistent with this invention may be provided.

While the invention has been described in connection with preferred embodiments, it also includes alternatives, modifications and equivalents within the spirit and scope of the appended claims.

What is claimed is:

1. A prosthesis comprising a cup member formed of resilient polymer encased in a metallic outer shell member, said cup member having an inner surface adapted to receive the male prosthetic member of an articulating joint and an outer surface comprising a spherical zone terminating at its base in a right cylindrical zone, the altitude of said spherical zone being less than the spherical radius, said cup member having an annular groove in the outer surface thereof disposed approximately at the junction of said spherical and cylindrical zones, said annular groove being canted toward the pole of said spherical zone, and said shell member having an outer surface adapted to be implanted in a skeletal cavity and an inner surface substantially congruent with the outer surface of said cup member, said inner shell surface having detent means for engaging said annular groove in said cup member to permanently secure said cup member within said shell member.

2. The prosthesis of claim 1 wherein said inner cup surface comprises a spherical zone concentric with said outer spherical cup surface having an altitude greater than the spherical radius of said inner cup surface.

3. The prosthesis of claim 1 wherein said outer shell surface comprises a spherical zone concentric with said inner spherical shell surface having an altitude greater than the spherical radius of said outer shell surface.

4. The prosthesis of claim 1 wherein said outer shell surface is adapted for implantation in the acetabulum.

5. The prosthesis of claim 1 wherein said outer shell surface comprises means to facilitate permanent attachment of said shell member to said skeletal cavity.

6. The prosthesis of claim 1 wherein said annular groove is canted at an angle of approximately 45 degrees toward said pole.

7. The prosthesis of claim 1 wherein said detent means comprises a plurality of projections distributed along the annular junction of the spherical and cylindrical zones of said congruent inner shell surface.

8. The prosthesis of claim 1 wherein said polymer is ultra high molecular weight polyethylene.

* * * * *

UNITED STATES PATENT AND TRADEMARK OFFICE
CERTIFICATE OF CORRECTION

PATENT NO. : 4,172,296
DATED : October 30, 1979
INVENTOR(S) : Joseph D'Errico

It is certified that error appears in the above-identified patent and that said Letters Patent are hereby corrected as shown below:

Column 4, line 14, "accomodate" should read --accommodate--.

Column 4, line 15, "mumber" should read --member--.

Column 4, line 66, "of primarily" should read --is primarily--.

Signed and Sealed this

Fifteenth Day of January 1980

[SEAL]

Attest:

SIDNEY A. DIAMOND

Attesting Officer

Commissioner of Patents and Trademarks